:United States Patent [19]

Sparks et al.

[11] Patent Number: 5,206,086
[45] Date of Patent: Apr. 27, 1993

[54] PARTICLE-STABILIZED EPITOPES FOR STANDARDIZATION AND CONTROL OF IMMUNOASSAYS

[75] Inventors: Charles E. Sparks; Janet D. Sparks, both of Pittsford; Michael R. Violante, Rochester, all of N.Y.

[73] Assignee: University of Rochester, Rochester, N.Y.

[21] Appl. No.: 108,260

[22] Filed: Oct. 13, 1987

[51] Int. Cl.$^5$ .................. B32B 33/00; G01N 33/543; C07K 17/02
[52] U.S. Cl. .................................. 428/403; 435/810; 436/518; 436/523; 530/402
[58] Field of Search ................. 436/825, 826, 518, 13, 436/523, 528, 529, 531, 533, 537; 435/5, 810; 530/402; 428/403

[56] References Cited

U.S. PATENT DOCUMENTS

| | | |
|---|---|---|
| 3,202,731 | 8/1965 | Lolle . |
| 3,802,909 | 4/1974 | Rockett et al. . |
| 3,937,668 | 2/1976 | Koogesleger et al. . |
| 4,094,965 | 6/1978 | Layne et al. . |
| 4,177,253 | 12/1979 | Davies ........................ 424/1 |
| 4,454,234 | 6/1984 | Czerlinski ............... 436/526 |
| 4,465,776 | 8/1984 | Cidlowski et al. ........... 436/504 |
| 4,607,009 | 8/1986 | Steplewski et al. ............... 435/7 |
| 4,745,075 | 5/1988 | Hadfield ...................... 436/523 |
| 4,826,689 | 5/1989 | Violanto ..................... 424/489 |
| 4,970,144 | 11/1890 | Fareed et al. ................... 435/5 |

OTHER PUBLICATIONS

Rosseneu et al. Some Considerations of Methodology and Standardization of Apolipoprotein B Immunoassays Clin. Chem vol. 29 pp. 427–433 (1983).
Naito, H. K. Reliability of Lipid and Lipoprotein Testing Amer. J. of Cardiology vol. 56, pp. 6J–9J (1985).
Cooper, G. R. et al. International Survey of Apolipoproteins A–I and B Measurements (1983–1984) Clin. Chem. vol. 30, pp. 223–228 (1985).
Hutchens, T. Protein Recognition of Immobilized Ligands: Promotion of Selective Adsorption Clin. Chem. vol. 33, pp. 1502–1508 (1987).
Geysen, et al. "Strategies for Epitope Analysis Using Peptide Synthes." J. Immunological Methods 102:259–274 (1987).
Walter, G. "Production and Use of Antibodies Against Synthetic Peptides" J. Immunological Methods 88 (1986) 149–161.
Higgins, I. J., in "Immobilized Cells and Enzymes," J. Woodward (ed.), IRL Press, Washington, D.C., (1985), p. 1.
Watt et al, Pharmac. Ther., vol. 28 pp. 29–50, 1985.
Marcel et al. Lipid Res. vol. 23 pp. 169–195, 1985.
Steinberg, et al Clin. Chem. vol. 29 pp. 415–426, 1983.

Primary Examiner—Christine M. Nucker
Assistant Examiner—M. P. Woodward

[57] ABSTRACT

The invention relates to a process for preparing standards and controls for immunoassays employing monoclonal antibodies. Monoclonal antibodies are used to isolate a restricted portion of an antigen containing an epitope that determines the specificity of the monoclonal antibody-antigen reaction so as to distinguish it from the antigen as a whole, following fragmentation of the complex antigen by procedures including proteolysis. Isolated epitopes are attached covalently or by physical adsorption to particles to immobilize and stabilize the epitope. The particles can be composed of iodipamide ethyl ester, polyvinyl chloride, polystyrene and other inert substances and can be chemically activated to improve epitope binding and stability. Experimental details demonstrate the binding of lipoprotein epitopes to IDE, polyvinyl chloride and polystyrene and the subsequent reaction of monoclonal antibodies to these particle-stabilized epitopes.

This invention is useful particularly for measuring the lipoprotein components associated with cholesterol, and includes a monoclonal based immunoassay kit for measuring the lipoprotein components in biological fluids to assess risk related to coronary artery disease complications.

19 Claims, No Drawings

PARTICLE-STABILIZED EPITOPES FOR STANDARDIZATION AND CONTROL OF IMMUNOASSAYS

BACKGROUND

Field of the Invention

Immunoassays of antigenic substances (antigens) present in biologic fluids are often used in the evaluation of physiologic or pathologic states in animals including humans. Components of immunoassays are the antigen and specific antibody, and the assay involves the binding of these components to each other in a way which is dependent on the concentration of each component.

An antigen has two properties: (1) the capacity to stimulate the formation of corresponding antibodies and (2) the ability to react specifically with the corresponding antibodies. Essentially all proteins, many polysaccharides, nucleoproteins, lipoproteins, synthetic polypeptides and smaller molecules, such as haptens, if linked to larger proteins, behave as antigens. A hapten is a small, incomplete antigen being incapable alone of causing the production of antibodies but capable of reacting with specific antibodies which are produced when the hapten, attached to a larger antigenic substance, is injected into an animal. Induction of antibody formation or immunization occurs when the antigen is introduced into a living body through the skin, muscle, intraperitoneal injection or intravenous injection. The ability of an antigen to stimulate antibody production is enhanced if the compound is retained in the tissues. Because of this finding, materials which allow for the slow release of the antigen for prolonged periods, also known as adjuvants, are used to increase the antibody response to antigen.

The ability to elicit an antibody response is dependent upon the biological system and conditions employed, dose, route of administration, etc. In response to an antigen, the animal produces antibodies which are capable of reacting to each and every site of the antigen it recognizes as foreign. The smallest portion of the antigen that can determine an antibody specificity is termed an antigenic determinant or epitope. The many antibodies produced against a given antigen is a result of a corresponding large number of different antibody-producing cell lines and are termed polyclonal antibodies or polyclonal antisera. Polyclonal antibodies are mixtures of many different antibody specificities against all the many antigens an animal has been exposed to in a lifetime. Because most of the antibodies present in antisera are not specific for any given antigen, there are difficulties associated with purifying antibodies specific for a given antigen. Polyclonal antibodies are extremely heterogeneous with respect to their affinities for antigen; the effects of temperature, pH and ionic strength on rates of immunoreaction and variability of the immune response to antigen from animal to animal. The use of monoclonal antibodies in the present invention, obtained by a process described by Kohler and Milstein in *Nature* 256 495–497, 1975, eliminates many problems associated with the heterogeneous nature of polyclonal antibodies and provides a homogeneous reagent that has a uniform binding affinity and specificity. A monoclonal antibody reacts with only a very small portion of the larger, more complex antigen called an antigenic determinant or epitope.

The presence of antigen in a biologic fluid can be estimated by comparing the reaction of the unknown sample to that of the same or similar antigen. By using standard quantities of antigen or standards in an immunoassay, the concentration of an unknown amount of antigen can be estimated by a process known as standardization. The reaction of the standards relate to their content of antigen and can be graphed on the Y-axis while their known antigen content can be graphed on the X-axis to produce a standard curve. The reaction of an unknown is then found on the Y-axis and used to fix a value for the unknown on the X-axis. This process of standardization relies on the similarity of reactivity of the standards added to the assay and the unknown antigen.

Standard antigens may be altered in their reactivity with a given antibody over time and therefore it is necessary to monitor or control the standardization process so that results of assays run at different times can be compared. This process of controlling immunoassays involves the assay of control samples which contain the antigen in a fluid similar to that of the test samples being measured. The control samples are assayed every time the assay is standardized and are assumed to react in a similar fashion over the course of time. Variability and trends in the assayed control values reflects differences in the standard curve which may occur due to deterioration of the standards. It is important to have stable materials for standardization and control of immunoassays to assure the reproducibility and accuracy of the immunoassay. Accuracy refers to the assessment of how close a value is to the true value while precision refers to the degree of spread of a series of observations or reproducibility where the spread is specifically stated, that is, within run precision, day-to-day precision, etc. These terms are discussed in detail by Theodore Colton in his book, *Statistics in Medicine*, Little, Brown and Company Publishers, p. 38 (1974). Controls and standards, therefore, become as important to the validity of any immunoassay as the antibody and the antigen.

Certain immunoassays are particularly difficult to standardize and control because the antigen of interest is unstable and does not show uniform reactivity to antibodies. Minor alterations of certain antigens as would be necessary for production of stable standards and controls may significantly alter the binding of antibody which is essential for immunoassay. Even more subtle changes may occur in the structure of antigens with respect to their tertiary or quaternary structure adversely affecting antibody-antigen reactions. A problem, therefore, exists in the preparation of controls and standards for certain immunoassays as it is necessary to store standards and particularly controls over extensive periods of time in order to be useful for the control of the accuracy and precision of the assay. The standards and controls must also be preserved in such a way that they maintain uniform reactivity with the antibody. This invention relates to a process whereby stable controls and standards are prepared which react uniformly with antibody and provide for the long-term standardization and control of immunoassays involving labile antigens.

One important aspect of this invention involves the isolation and purification of specific epitopes for use as standards and controls in immunoassays involving monoclonal antibodies. Monoclonal antibodies are specific for epitopes which are normally present only once, but can be repetitive on certain antigens. Epitopes of proteins may be as small as 5 to 7 amino acid residues and may represent a specific linear amino acid sequence or a spatial arrangement of amino acids dependent upon conformation. Using a monoclonal antibody of suitable affinity the corresponding epitope may be isolated and purified from a mixture of antigens or from modified or fragmented antigen. Generally, the larger the antigen, the more likely it is to be unstable and degraded into fragments or smaller pieces. Since epitopes are always smaller than the intact antigen, epitope stability is invariably greater than the stability of the native antigen. While polyclonal antibodies may be greatly affected by the breakdown of the native antigen, carefully selected monoclonal antibodies, particularly those reactive with a specific amino acid sequence, may remain unaffected because the epitope being defined by the monoclonal antibody resides completely within a fragment of the native antigen. An important aspect of this invention is selecting monoclonal antibodies whose epitopes are not destroyed after fragmentation of the native antigen.

The binding of substances to surfaces enhances the stability of that substance. Antigens and/or antibodies have been bound to solid surfaces previously in the prior art to facilitate the separation of antibody-bound antigen from free antigen following reaction. An important distinction in this invention is the binding of an antigen and/or epitope to particles so that the bound epitope is stabilized in such a way as to make it useful in the preparation of standards and controls for immunoassays. Additionally, the stabilization of epitopes on particles allows for a much larger surface area and a much higher concentration of epitope for subsequent reaction. This significantly reduces reaction time and makes kinetic assays practical.

There is a well recognized relationship between the amount of cholesterol in the blood and atherosclerosis or coronary artery disease as reported in the *Complete Home Medical Guide*, of the Columbia University College of Physicians and Surgeons, [Crown Publishers, page 367, 1985]. Since cholesterol is a fatty substance (lipid) that is not soluble in blood, which is mostly water (and fats and water do not mix), cholesterol must associate with a detergent-like substance before it can travel through the blood. One such substance is a protein designated an apolipoprotein, which, when combined with lipid, forms a molecule called a lipoprotein. There are different types of lipoproteins, which are often classified by their size or density as determined by high-speed centrifugation (ultracentrifugation). The heaviest is high-density lipoprotein (HDL), which has the highest proportion of protein. Low density lipoprotein (LDL) is lighter than HDL, and carries a larger proportion of cholesterol. Very low density lipoprotein (VLDL) carries the largest proportion of triglyceride, a lipid that is important in fat metabolism. Recent studies suggest that HDL carries cholesterol away from arterial cells and is therefore important in balancing the accumulation of cholesterol and other fats within arteries. LDL carries cholesterol to arterial cells and is believed to be a major factor in the development of atherosclerosis. Thus, in blood plasma a high level of HDL cholesterol in relationship to LDL cholesterol, is now considered desirable. The higher the ratio of HDL to LDL cholesterol, the better.

Recent evidence indicates that the quantity of the major apolipoproteins of HDL (apolipoprotein A-I, apo AI) and LDL (apolipoprotein B, apo B) or apolipoproteins A-I and B (apo A-I and apo B), respectively, are even better measures of risk of developing heart attack than the measurement of HDL and LDL cholesterol. There is a strong correlation (positive) with apo B (LDL) and an inverse correlation (negative) with apo A-I (HDL) with respect to risk of developing clinically manifest coronary heart disease. Further refinements of the methods of quantitative determination of the associated apolipoproteins is expected to lead to the identification of more precise relationships relating to the causation of heart attacks in humans.

A particular problem in immunoassays involving lipoprotein apolipoprotein is the number of reactions that are well known to occur which alter protein structure and conformation of apolipoprotein antigens which may alter immunoreaction. Such reactions include lipid peroxidation, protein fragmentation due to peroxides and oxygen, enzymatic fragmentation and aggregation. Any of these reactions may adversely affect the immunoassay of apo B and apo A-I. There is a critical need for an improvement in standardizing and controlling assays involving apo B and apo A-I because they are particularly labile. Alteration of their lipid environment is well known to change conformation and immunoreactivity. Accordingly, one important aspect of this invention is to provide particle-stabilized epitopes specific for apo B and apo A-I for use as standards and controls in immunoassays of these important components of LDL and HDL.

SUMMARY OF THE INVENTION

This invention relates to a process for producing controls and standards for use in immunoassays for the determination of the presence and concentration of antigens in blood plasma or other biological fluids but is not limited to biological fluids. More particularly, this invention relates to the production of particle-stabilized epitopes of antigens which are known to be associated with specific physiological and biochemical disorders. Controls and standards are prepared so as to allow them to react uniformly with the antibody and provide for long-term standardization and control of immunoassays. According to the present invention, a small fragment of a large, more complex antigen, retaining an antigenic determinant or epitope defining a monoclonal antibody specificity, is produced. Since epitopes are smaller than the native antigen, epitopes are more stable than antigen. One important aspect of this invention, therefore, involves the isolation and purification of specific epitopes to be used as standards and controls in immunoassays involving monoclonal antibodies. The epitope can be a chemically modified antigen or an antigen which is chemically or biologically synthesized. The epitope may consist of a protein, peptide, carbohydrate, lipoprotein, protein-carbohydrate complex, lipid-protein-carbohydrate complex, immunoglobulin, nucleic acid or other antigenic material or hapten. The fragment containing the epitope in question is attached, covalently or by physical adsorption, to particles composed of material such as iodipamide ethyl ester, polyvinyl chloride or polystyrene so as to render the epitope stable. Multiple epitopes may be attached to the same or different particles for the control and standardization of more than one assay.

DETAILED DESCRIPTION OF THE INVENTION

This invention relates to a process for producing controls and standards for use in immunoassays for the determination of the presence and concentration of antigens in blood plasma or other biological fluids but not limited to biological fluids. More particularly, this invention relates to the production of particle-stabilized epitopes of antigens which are known to be associated with specific physiological and biochemical disorders. Controls and standards are prepared so as to allow them to react uniformly with the antibody and provide for long-term standardization and control of immunoassays. The process for producing stable controls and standards comprises: (1) selecting a monoclonal antibody which is a product of a single cell line which retains reactivity to the epitope after the epitope is attached to particles; (2) isolating the epitope; (3) stabilizing said epitope by attachment to particles; (4) preparing particle-stabilized epitopes as standards by diluting in buffered aqueous vehicles to known concentrations in the range of 0.01 to 10 times the normal value of said antigenic substances and (5) preparing particle-stabilized epitopes as control samples by suspending in a fluid which mimics the composition of the test sample but contains no other epitope reactive to said monoclonal antibody.

The epitope is a determinant of an antigenic substance, selected from the group consisting of the intact antigen, chemically modified antigen, antigen fragment, chemically synthesized antigen, biologically synthesized antigen and hapten, which retains the ability to react with said monoclonal antibody. The antigenic substance is selected from the group consisting of a protein, peptide, carbohydrate, protein-carbohydrate complex, lipid-protein-carbohydrate complex, immunoglobulin and nucleic acid. The epitope may be derived from a lipoprotein selected from the group consisting of high density lipoprotein, low density lipoprotein and very low density lipoprotein.

In this invention, the monoclonal antibody is used to isolate its corresponding epitope which can consist of a partial antigen, or may comprise a very small portion of the entire antigen. The epitope, because of the way in which it is isolated, is guaranteed of reactivity with the antibody. Epitopes may be purified by means other than binding to the monoclonal antibody so long as the purified epitopes maintain reactivity with the antibody. Epitopes can be isolated using the monoclonal antibody following preliminary isolation by chromatography, electrophoresis, and other known techniques of separation. The epitope of interest is then attached, covalently or by physical adsorption, to particles composed of material such as iodipamide ethyl ester, polyvinyl chloride or polystyrene. The particles may be chemically modified so as to be active in the binding of the epitope. Binding of the epitope renders the epitope stable. Although the particles can consist of many kinds of material, certain materials may be particularly useful for the process which have designated physical properties of size, density and chemical composition so as to facilitate the actual immunoassay. Particle materials can be chemically activated to optimize attachment of epitopes and their subsequent stabilization. The particles are composed of a substance selected from the group consisting of latex, starch, resin, ester, organic acids and organic bases which are insoluble in biological fluids. We provide examples for the use of iodipamide ethyl ester (IDE) as the particle material. This material is shown to bind epitopes of apolipoproteins in such a way as to maintain reactivity with the monoclonal antibody. This material has the desirable property of having increased density which facilitates separation from the biologic fluid. Particles with densities in the range of 0.1 to 10 g l cc have proven useful for this invention. Particles having mean diameters in the range of 1 to 100,000 nanometers with a coefficient of variation of less than 25% can be chosen to maximize the kinetics of interaction of epitope and antibody at any known concentration of antibody. Stabilized epitopes on these particles affords unique properties for use in specialized immunoassays particularly applicable to lipoproteins where the particles can be made the size of lipoproteins for control and standardization of apolipoprotein immunoassays. The clear advantage is that the particle material is inert whereas the lipid core of a lipoprotein is unstable.

The immunoassay is standardized by adding known concentrations of particle-stabilized epitopes and titrating them against a finite amount of monoclonal antibody or a monoclonal antibody mixture. In so doing the immunoreaction for each standard is used to develop a standard curve which allows an estimation of unknown amounts of antigen in a biologic fluid by comparison. For control samples, the epitope is prepared in an environment similar to the biologic fluid being measured and is assayed as if it were an unknown sample. For the assay of samples of serum, control samples consist of particle-stabilized epitopes in serum from an animal species different than the one from which the epitopes were derived. Monoclonal antibodies are chosen that are species specific, that is, specific for human antigen but not the corresponding bovine antigen. Because the standards and controls are prepared from particle-stabilized epitopes, they maintain their reactivity over time. Supplies of standards and controls can be stored in a frozen or freeze-dried or lyophilized state and be reconstituted as needed.

Since epitopes are small, many identical epitopes can be attached to the particle surface to optimize the physical interaction between epitope and monoclonal antibody. In another instance, several distinct epitopes of the same antigen defined by additional monoclonal antibodies can be attached to the particle surface. In yet another instance, multiple epitopes from several different antigens can be attached to the particle surface and used as standards for several immunoassays. These assays work because particle-stabilized epitopes have the properties of the intact antigen in terms of interacting with the antibody, but have lost the property of being susceptible to alteration within the environment. Finally, multiple epitopes derived from distinct antigenic substances can be stabilized on mixtures of particles differing in physical properties including size, density, composition and appearance, to facilitate separation of these said epitopes after reaction with their respective monoclonal antibodies. Therefore, one sample of such particles could serve as controls and standards for a number of different immunoassays.

EXAMPLES

The following examples are offered by way of illustration and not by way of limitation.

(1) Epitope-specific Monoclonal Immunoassay of Apolipoprotein B Bound to IDE Particles a) Preparation of Low Density Lipoprotein (LDL)

Very low density lipoprotein (VLDL) was isolated from human serum by high-speed centrifugation of the serum at an average of 175,000×g for 16 hours at 14° C. after serum was adjusted to a salt density of 1.019 g/ml by dissolving 0.177 g sodium bromide per 10 ml of serum. The cloudy supernatant containing VLDL was removed, and the infranatant was readjusted to a salt density of 1.063 g/ml by dissolving an additional 0.608 g of solid sodium bromide per ml. Low density lipoprotein (LDL) was isolated by centrifugation at an average of 175,000×g for 18 hours at 14° C. The yellow LDL supernatant layer was removed. Greater than 95% of the protein in the LDL fraction was apolipoprotein B (apo B). Salts were removed from the LDL preparation by dialysis against 0.15M NaCl using a semi-permeable cellulose membrane excluding compounds of greater than 3500 dalton molecular weight.

b) Preparation of Mouse Anti-human LDL Monoclonal Antibodies

Two, four week old mice were immunized by subcutaneous injection of 0.5 ml of 100 μg of LDL emulsified in a total volume of 0.5 ml of mineral oil containing suspended tubercle bacilli (Freund's complete adjuvant). Mice were reimmunized three weeks later by subcutaneous injection of an emulsion of 100 μg of LDL and mineral oil in a total volume of 0.5 ml. Three weeks later serum was obtained from the tail vein and both mice showed evidence of specific antibody production against human apo B. [See Table I]. The mouse with the highest concentration of specific antibody against apo B was reimmunized several times the week prior to the hybridization of its spleen cells with myeloma cells (fusion). Several days prior to hybridization, 1 μg of LDL was injected intraperitoneally. Four days prior to fusion 100 μg of LDL was given intraperitoneally; three days prior to fusion 200 μg of LDL was given intraperitoneally and intravenously; two days prior to fusion 100 μg of apo B was given intravenously and one day prior to fusion 200 μg of human apo B was given intraperitoneally and intravenously. One day after the last injection the mouse was killed and its spleen was removed and dispersed into a single cell suspension in nutrient broth containing 10%, v/v, fetal calf serum (media). Spleen cells were washed once with media and were mixed with myeloma cells derived from the cell line, P3-X63-Ag 8.653, which is on deposit at the American Type Culture Collection, at a ratio of between 1 and 10 spleen cells to 1 myeloma cell in the presence of polyethylene glycol. The fusion process was similar to that described by Kohler and Milstein and reported in *Nature* 256, 495–497 (1975). After the cells were hybridized, fused cells (spleen and myeloma) or hybridomas, were washed and suspended in media which selectively allows for the growth of hybridomas but not myeloma cells, and then added to 96 well dishes. Hybridoma growth was enhanced by regularly adding to the culture, at a concentration of $10^6$ cells per well, peritoneal macrophages obtained from sterile saline washings of the peritoneal cavity of other mice. Proliferating hybridomas were recognized by their distinctive morphology. After significant growth the media above the cells or culture supernatant was tested for the production of specific antibody to human LDL, [See Table II]. Hybridomas secreting monoclonal antibodies against human LDL were counted, diluted in media, and recultured in 96 well dishes at a concentration of 1 cell per 2 wells to assure that subsequent growth of antibody producing cells were the progeny of a single cell hybridoma or clone. Culture supernatants of monoclonal antibody producing clones were retested at intervals for the presence of specific antibody against human LDL. Five clones retained specific antibody production (Table II). These cell lines were expanded by growing them first in 24 well dishes, then in 50 ml flasks and later in 275 ml flasks. Approximately $10^6$ hybridoma cells from each of the five clones were injected intraperitoneally into mice which had been previously treated with 0.5 ml of 2,6,10,14-tetramethylpentadecane (pristane) at least one week prior to injection of hybridomas. Ascites tumors appeared in about one month and ascitic fluid was collected and contained 22–35 mg/ml monoclonal antibody specific for human LDL.

c) Screening for Mouse Anti-human LDL Monoclonal Antibodies

Polyclonal antibodies against human LDL in mouse sera collected from immunized mice and monoclonal antibodies in culture supernatants in which hybridomas were grown were assayed in the following manner. Human LDL was prepared as outlined in 1a, diluted to a concentration of 10 μg/ml in 0.15M sodium carbonate/0.035M sodium bicarbonate buffer, pH 9.0., and then 0.1 ml of the diluted LDL was added to each well of a 96 well plate and incubated overnight at 4° C. After incubation the liquid from each well was removed by aspiration. The wells were washed three times with 0.2 ml of 1%, w/v, bovine serum albumin (BSA) dissolved in 0.15M NaCl/0.05M phosphate buffer, pH 7.4 (phosphate buffered saline or PBS). After washing, the wells were filled with 0.25 ml of 1%, w/v, BSA in PBS and incubated at room temperature for 2–4 hours. Afterwards, the liquid in each well was removed and 0.1 ml of diluted mouse sera from immunized mice [Table I] or 0.1 ml of media from culture supernatants of hybridomas [Table II] was added to the wells and incubated overnight at 4° C. The liquid from each well was removed by aspiration. To each well was then added 0.1 ml of $^{125}$I-labeled sheep anti-mouse antibody diluted in 1%, w/v, BSA, in PBS containing 600,000 disintegrations per minute per ml, (DPM/ml). Wells were incubated for 4 hours at room temperature. The liquid from each well was removed by aspiration and wells were washed three times with 0.2 ml of 1%, w/v, BSA in PBS. Radioactivity, (DPM), bound to each well representing mouse antibody reacted to human LDL was radioassayed and results are set forth in Table I and Table II. Table I summarizes results obtained when mice are injected with human LDL as an antigen. Preimmune serum refers to assay results obtained before the mice were injected with LDL and immune serum refers to results obtained after injection with LDL. The screening assay for mouse antibody is run on dilutions of serum (1:10, 1:100 and 1:1000). As seen in Table I, mouse 1 had a 43-fold increase in bound DPM (preimmune versus immune serum) using serum diluted 1:1000 whereas mouse 2 had a 38-fold increase in bound DPM (pre-immune versus immune serum) using serum diluted 1:1000. The results indicated both mice were highly immunized against human

TABLE I

Mouse Polyclonal Antibody Production Against Human Apo B, DPM/well

| | Mouse 1 | | Mouse 2 | |
|---|---|---|---|---|
| Dilution | Pre-Immune Serum | Immune Serum | Pre-Immune Serum | Immune Serum |
| 1:10 | 220 | 6865 | 224 | 7115 |
| 1:100 | 254 | 9470 | 203 | 8492 |

TABLE I-continued

| | Mouse Polyclonal Antibody Production Against Human Apo B, DPM/well | | | |
|---|---|---|---|---|
| | Mouse 1 | | Mouse 2 | |
| Dilution | Pre-Immune Serum | Immune Serum | Pre-Immune Serum | Immune Serum |
| 1:1000 | 221 | 9576 | 210 | 8164 |

Table II summarizes results obtained when culture supernatants of 5 clones of hybridomas prepared from the spleen of mouse 1 (Table I) were tested for production of monoclonal antibody. The presence of antibodies specific for human LDL are indicated by a 5 to 10-fold increase over the negative control of radioactivity bound to the LDL-coated wells. Each of the five clones indicated in Table II represents cells producing a single monoclonal antibody against human apo B.

TABLE II

| Screening For Mouse Monoclonal Antibody Production Against Human Apo B, DPM/well | | | | | |
|---|---|---|---|---|---|
| Negative | Clone 1 | Clone 2 | Clone 3 | Clone 4 | Clone 5 |
| 579 | 4009 | 3121 | 4119 | 2961 | 3040 | d) Determination of Mouse Anti-human Apo B Monoclonal Antibody Specificity

Lipid was removed from LDL by diluting 1.0 ml of LDL in a solution of 10 ml chloroform, 10 ml methanol and 20 ml diethyl ether at 4° C. Apolipoprotein B (apo B) of LDL formed a white precipitate which was collected by centrifugation at 10,000×g for 20 min at 4° C. The precipitate was washed once with 20 ml of diethyl ether and diethyl ether was removed by aspiration. The precipitate was warmed to about 35° C. to remove residual diethyl ether, and then dissolved in a solution of 0.067M 2-amino-2-hydroxymethyl-1,3-propanediol/HCl buffer, (Tris buffer), pH 6.8 containing 2%, w/v, sodium dodecyl sulfate, SDS, 10%, v/v, glycerol and 5%, v/v, 2-mercaptoethanol. After dissolving the apo B precipitate, the solution was heated to 100° C. for 3 minutes and allowed to cool to room temperature. Proteins in the solution were separated according to molecular weight by electrophoresis in a 1.5 mm thick rectangular gel polymerized from a solution containing 0.26%, w/v, N,N'-methylenebisacrylamide and 2.85%, w/v, acrylamide, 0.375M 2-amino-2-hydroxymethyl-1,3-propanediol/HCl buffer, pH 8.8, 2%, w/v, sodium dodecyl sulfate 0.025%, w/v, ammonium persulfate and 0.5 µl/ml N,N,N',N'-tetramethylethylenediamine. The reservoir buffer contained 0.025M 2-amino-2-hydroxymethyl-1,3-propanediol/HCl buffer, pH 8.3 containing 0.192M glycine and 1%, w/v, sodium dodecyl sulfate. The protein solution was applied at the edge of the rectangular gel and apo B and apo B fragments were separated in one dimension by electrophoresis at 150 V for four hours while the reservoir buffer was cooled to 7° C. After electrophoretic separation the rectangular gel containing the separated proteins was submerged in a buffer containing 0.30%, w/v, 2-amino-2-hydroxymethyl-1,3-propanediol, 1.44%, w/v glycine and 20%, v/v, methanol for 10 minutes with agitation. This process was repeated three times to remove sodium dodecyl sulfate and salts from the acrylamide gel. Then a solid sheet of rectangular nitrocellulose fibers of the same size as the rectangular gel and preincubated in the same buffer was placed in close contact with the acrylamide gel. Air bubbles were removed and the two components were squeezed together by rolling a test tube across the surface to form a nitrocellulose acrylamide-gel sandwich. Proteins separated on the acrylamide gel were then transferred from the acrylamide gel to the nitrocellulose fiber by placing the sandwich in an electrophoresis chamber and electrophoresing in a perpendicular field at 0.1 amps for 16 to 18 hours in a buffer composed of 0.30%, w/v, 2-amino-2-hydroxymethyl-1,3-propanediol, (Tris), 1.44%, w/v glycine and 20%, v/v, methanol precooled to 4° C. After the proteins were transferred to the nitrocellulose fibers a thin strip was cut and stained in napthol blue black (C.I. 20470; amido black 10B; Buffalo Black NBR) to visualize the placement of the protein bands for reference later. The remaining sheet was incubated in 3%, w/v, gelatin in 0.15M NaCl, 0.02M Tris buffer, pH 7.5 containing 0.05%, v/v, Tween 20 overnight at room temperature in order to bind any remaining protein binding sites on the nitrocellulose sheet. Thin strips were cut from the gelatin-treated sheet of nitrocellulose containing the transferred proteins and incubated with the culture supernants of individual hybridoma clones overnight in a buffer containing 1%, w/v, gelatin in 0.15M NaCl, 0.02M Tris buffer, pH 7.5. After incubation, the strips were washed three times in 0.15M NaCl, 0.02M Tris buffer pH 7.5 containing 0.05%, v/v, Tween 20 and then incubated for 4 hours at room temperature in an alkaline phosphatase conjugated goat anti-mouse antibody. The strips were washed three times in 0.15M NaCl, 0.02M Tris buffer, pH 7.5 and then binding of the monoclonal antibody to the transferred protein bands was detected by a final incubation in an alkaline phosphatase substrate to detect binding of the alkaline phosphatase conjugated goat anti-mouse antibody reaction. The alkaline phosphatase substrate solution contained 15 mg 5-bromo-4-chloro-3-indolyl phosphate dissolved in 1.0 ml of N,N-dimethylformamide and 30 mg nitro blue tetrazolium or 2,2'-Di-p-nitrophenyl-5,5'-diphenyl-3,3'-[3,3'-dimeth-oxy-4,4'-diphenylene]ditetrazolium chloride dissolved in 1.0 ml of 70%, v/v, N,N-dimethylformamide in 100 ml 0.1M sodium bicarbonate, 1 mM magnesium chloride. Apo B specificity was determined by development of colored apo B bands which had been transferred to nitrocellulose having the characteristic molecular weight of apo B.

e) Binding of Apolipoprotein B (Apo B) to Iodipamide Ethyl Ester (IDE)

Iodipamide ethyl ester (IDE) particles were prepared by infusing two parts of an aqueous solution (0.1%, w/v) of polyvinyl pyrrolidone (15,000 MW) at a rate of 5 ml/minute into a cold (4° C.), rapidly stirred solution of one part IDE (5%, w/v) in dimethyl sulfoxide (DMSO) and one part ethanol. Immediately after formation of the particles 1.0 ml of human low density lipoprotein $^{125}$I-labeled apo B of a known protein specific activity [disintegrations per minute per mg protein], and at concentrations between 0.4 microgram and 641 micrograms of protein per ml was added to 1.0 ml of IDE particles. The particles and protein were mixed and then the particles were washed by addition of 0.15M NaCl, 0.05M sodium phosphate, pH 7.4 (PBS) containing human serum albumin at a concentration of 0.1%, w/v. After centrifugation, the washing solution was removed by aspiration and the particles were resuspended and washed again until radioactivity released into the wash solution was negligible (about four washes). The $^{125}$I-labeled apo B bound to the IDE particles was then radioassayed and the mass of apo B bound by the IDE particles was calculated using the specific activity of the original $^{125}$I-labeled apolipoprotein B. The results are set forth in Table III.

TABLE III

Apolipoprotein B Bound to Iodipamide Ethyl Ester Particles

| Micrograms Added | Micrograms Bound |
|---|---|
| 0.4 | 0.14 |
| 1.0 | 0.23 |
| 1.5 | 0.28 |
| 2.0 | 0.43 |
| 2.5 | 0.46 |
| 4.5 | 1.0 |
| 10 | 3.7 |
| 15 | 5.9 |
| 20 | 6.1 |
| 40 | 9.3 |
| 116 | 59.0 |
| 191 | 63.0 |
| 341 | 81.0 |
| 491 | 114.0 |
| 641 | 130.0 | f) Immunoassay of Apo B/IDE Particles Using Flow Cytometry

Iodipamide ethyl ester (IDE) particles coated with human apo B (B/IDE particles) were reacted with monoclonal antibodies whose specificities for apo B were determined as described in 2(d). The B/IDE particles were incubated overnight at 4° C. with the culture supernatants of two hybridoma clones secreting unique monoclonal antibodies designated 185. and 208. After incubation, the particles were washed in PBS containing 0.1%, w/v, bovine serum albumin (BSA) three times. The B/IDE particles were then incubated for three hours at room temperature with sheep anti-mouse antibody covalently attached to biotin (hexahydro-2-oxo-1H-thienol[3,4-d]imidazole-4-pentanoic acid). After incubation the particles were washed three times in 0.1%, w/v, BSA in PBS and then incubated with avidin covalently modified with fluorosceinisothiocyanate for 30 minutes at room temperature. Fluorosceinlabeled avidin forms a very strong complex with biotin rendering the particles that contain the bound sheep anti-mouse antibodies fluorescent. Therefore, particles with attached apo B that reacted with mouse monoclonal antibodies are fluorescent. The B/IDE particles were washed three times in a buffer containng 0.1%, w/v, BSA and then fluorescent particles were analyzed using fluorescence-activated flow cytometry. Results are set forth in Table IV.

TABLE IV

Anti-Human Apo B Monoclonal Antibody Reactivity to B/IDE Particles Using Fluorescence Activated Flow Cytometry

| Preparation | Mean Channel |
|---|---|
| B/IDE Particles Only | 29.8 |
| Negative Staining Control | 35.0 |
| Irrelevant Monoclonal Antibody | 35.3 |
| Monoclonal Antibody-human Apo B (185) | 52.1 |
| Monoclonal Antibody-human Apo B (208) | 53.1 |

The fluorescence of the B/IDE particles are assessed on a fluorescence per particle basis using this method and results are expressed as the mean channel (average) of fluorescence representing the average fluorescence per particle. The higher the channel the more the fluorescence per particle and the more monoclonal antibody bound to the particles. The scale, however, is not linear but is a logarithmic scale. The difference in the mean channel of the negative staining control, B/IDE particles alone (no antibody) and reaction with irrelevant monoclonal antibody compared to the reaction with monoclonal antibodies specific for human apo B (185. and 208.) was 18. These results clearly demonstrate that (1) apo B was attached to the IDE particles; (2) the monoclonal antibodies reacted to the B/IDE particles and (3) the reaction is specific for anti-human apo B monoclonal antibodies because of the lack of reaction of the particles with an irrelevant monoclonal antibody. This example demonstrates that an epitope of a larger antigen can be attached to a particle surface in such a way that its reactivity for specific monoclonal antibodies is retained.

(2) Epitope-specific Monoclonal Immunoassay of Apo B Bound to Polyvinyl chloride All of the following were performed in accordance with the procedures outlined in Example (1). LDL was isolated from human serum by high speed centrifugation and mouse anti-human LDL monoclonal antibodies were prepared from mice immunized with human LDL. Hybridomas were screened for specific monoclonal antibody production to human LDL and apo B specificities of the monoclonal antibodies so produced were determined as described in example 1d.

a) Binding of Apo B to a Polyvinyl Chloride

Labeled $^{125}$I-apo B of a known protein specific activity [disintegrations per minute per mg protein, DPM/mg] and at concentrations between 0.49 mg/ml and 3.9 mg/ml in phosphate buffered saline (PBS) was added to a 7.1 mm$^2$ surface of polyvinyl chloride and incubated overnight at 4° C. The fluid was removed and the surface washed three times in 1%, w/v, bovine serum albumin (BSA) in PBS. After removing the washing solution by aspiration, the surface was radioassayed and the mass of apo B bound by the polyvinyl chloride was calculated using the specific activity of the original $^{125}$I-apo B. Results are set forth in Table V.

TABLE V

Binding of Human Apolipoprotein B to Polyvinyl Chloride

| Micrograms Added | Micrograms Bound |
|---|---|
| 0.49 | 0.025 |
| 0.98 | 0.045 |
| 1.95 | 0.080 |
| 3.90 | 0.138 | b) Immunoassay of Epitopes of Apo B

A 7.1 mm$^2$ polyvinyl chloride surface was incubated with human LDL at a concentration of 1.5 µg/ml dissolved in 0.15M sodium carbonate/0.35M sodium bicarbonate, pH 9.0 at 4° C. After incubation the surface was washed three times in a solution of 1%, w/v, BSA in PBS and incubated in the same solution for 2 hours at room temperature. After incubation the liquid from the surface was removed by aspiration and 0.1 ml of mouse anti-human apo B monoclonal antibody culture supernatant of a hybridoma clone, (5.01), diluted 1: 750 in 1% BSA in PBS was added. Immediately thereafter, 0.1 ml of human LDL diluted in 1%, w/v, BSA in PBS was added containing between 10 and 100 ng of apo B to compete with the apo B epitopes attached to the polyvinyl chloride surface. The mixture was incubated for 16 hours at 4° C. and then the surface was washed three times in 1%, w/v, BSA in PBS. Monoclonal antibody reacting with the apo B of LDL was removed by washing the surface and monoclonal antibody reactive to apo B epitopes attached to the polyvinylchloride was detected by a final incubation with $^{125}$I-labeled sheep anti-mouse antibody. Results of the competitive immunoassay of polyvinyl chloride-stabilized epitopes of apo B are presented below in Table VI. The more added LDL-apo B, the less radioactivity is bound to the polyvinyl chloride stabilized apo B epitopes. The percent of total counts added (Y-axis) can be graphed against the amount of added LDL-apo B (X-axis) to construct a standard curve. For samples containing an unknown amount of apo B, the calculated percent of total added counts found for the test sample is used to fix a value for the apo B content of the unknown.

TABLE VI

Competitive Immunoassay of Apo B Bound to a Polyvinyl Chloride Surface and Human LDL Apo B Using an Anti-human Apo B Monoclonal Antibody

| (ng) LDL | DPM Bound | Average DPM | % Total Counts |
|---|---|---|---|
| 0 | 5257, 5280 | 5267 | 100.0 |
| 5 | 4688, 4534 | 4611 | 87.5 |
| 10 | 4547, 4336 | 4442 | 84.3 |
| 20 | 3909, 3752 | 3831 | 72.2 |
| 30 | 3545, 3479 | 3512 | 66.7 |
| 40 | 2992, 2945 | 2969 | 56.4 |
| 50 | 2676, 2667 | 2672 | 50.7 |
| 75 | 2245, 2352 | 2299 | 43.6 |
| 100 | 2146, 2057 | 2102 | 39.9 |

(3) Binding of Apo B Epitopes to Polystyrene Particles

LDL was isolated from human serum by high speed centrifugation in accordance with the procedures outlined in Example 1a. Labeled $^{125}$I-apo B of a known protein specific activity (disintegrations per minutes per mg protein, DPM/mg) was used to assess the binding of apo B epitopes to polystyrene particles having a diameter of 3 mm and surface area of 2.8 mm$^2$. The particles were incubated in a 1.0 ml solution of 50 to 150 μg $^{125}$I-labeled apo B per ml PBS overnight at 4° C. After incubation the particles were washed three times and bound $^{125}$I-apo B was radioassayed. The mass of apo B bound by the polystyrene particles was calculated using the specific activity of the original $^{125}$I-apo B and the results are set forth in Table VII.

TABLE VII

Binding of Human Apolipoprotein B to a Polystyrene Particles

| Micrograms Added | Micrograms Bound |
|---|---|
| 50 μg/ml | 0.255 μg |
| 100 μg/ml | 0.636 μg |
| 150 μg/ml | 1.102 μg |

(4) Epitope-specific Monoclonal Immunoassay of Apo A-I Bound to IDE Particles a) Preparation of High Density Lipoprotein (HDL)

Very low density lipoprotein (VLDL) and low density lipoprotein (LDL) were removed from human serum by high-speed centrifugation of the serum at an average of 175,000×g for 18 hours at 14° C. after serum was adjusted to a salt density of 1.063 g/ml by dissolving 0.788 g sodium bromide per 10 ml of serum. The cloudy supernatant containing VLDL and LDL was removed, and the infranatant was readjusted to a salt density of 1.21 g/ml by dissolving an additional 2.145 g sodium bromide per 10 ml. High density lipoprotein (HDL) was isolated by centrifugation at an average of 175,000×g for 40 hours at 14° C. The HDL supernatant layer was removed and salts were eliminated from the HDL preparation by dialysis against 0.15 M NaCl using a semi-permeable cellulose membrane excluding compounds of greater than 3500 dalton molecular weight.

b) Preparation of Mouse Anti-human HDL Monoclonal Antibodies

Two, four week old mice were immunized by subcutaneous injection of 0.5 ml of 100 μg of HDL emulsified in a total volume of 0.5 ml of mineral oil containing suspended tubercle bacilli. Mice were reimmunized three weeks later by subcutaneous injection of an emulsion of 100 μg of HDL and mineral oil in a total volume of 0.5 ml. Three weeks later serum was obtained from the tail vein to test for evidence of specific antibody production against human HDL as described in example 4d. The mouse with the highest concentration of specific antibody production against HDL was reimmunized several times the week before its spleen cells were hybridized with myeloma cells (fusion). Several days prior to hybridization 1 μg of HDL was injected intraperitoneally. Four days prior to fusion 100 μg of HDL was given intraperitoneally; three days prior to fusion 200 μg of HDL was given intraperitoneally and intravenously; two days prior to fusion 100 μg of HDL was given intravenously and one day prior to fusion 200 μg of human HDL was given intraperitoneally and intravenously. Monoclonal antibodies were prepared in accordance with the procedures outlined in example 1b.

c) Screening for Mouse Anti-human HDL Antibodies

Antibodies against human HDL from mouse serum collected from immunized mice and secreted into the media in which hybridomas were grown were assayed in the following manner. Human HDL was prepared as outlined in example 4a and was diluted to a concentration of 10 μg/ml in 0.15M sodium carbonate/0.035M sodium bicarbonate buffer, pH 9.0. Exactly 0.1 ml of the diluted HDL was added to each well of a 96 well plate. After overnight incubation at 4° C., the liquid from each well was removed by aspiration. The wells were washed three times with 0.2 ml of 1%, w/v, bovine serum albumin (BSA) dissolved in 0.15M NaCl/0.05M phosphate buffer, pH 7.4 (phosphate buffered saline or PBS). After washing, the wells were filled with 0.25 ml of 1%, w/v, BSA in PBS and incubated at room temperature for 2-4 hours. Afterwards, the liquid in each well was removed and 0.1 ml of diluted mouse sera from immunized mice [Table VIII] or 0.1 ml of culture media from hybridomas [Table IX] was added to the wells and the wells were incubated overnight at 4° C. Afterwards the liquid from each well was removed by aspiration. To each well was added 0.1 ml of $^{125}$I-labeled sheep anti-mouse antibody diluted in 1%, w/v, BSA in PBS containing approximately 600,000 DPM/ml (disintegrations per minutes per ml). Wells were incubated for 4 hours at room temperature. The liquid from each well was removed by aspirations and wells were washed three times with 0.2 ml of 1%, w/v, BSA in PBS. Radioactivity (DPM) bound to each well representing mouse antibodies bound to human HDL was radioassayed and results are set forth in Table VIII and IX. Table VIII summarizes results obtained when mice are injected with human HDL as an antigen. Pre-immune serum results refers to assayed antibodies obtained before the mice were injected with HDL and the immune serum results refers to assayed antibodies obtained after injection with HDL. The screening assay for mouse antibody production is performed on dilutions of serum (1:10, 1:100, 1:1000, 1:2500, 1:5000, and 1:10,000). As seen in Table VIII, mouse 1 had a 31-fold increase in bound DPM (pre-immune versus immune serum) using serum diluted 1:10,000 whereas mouse 2 had a 13-fold increase in bound DPM (pre-immune versus immune serum) using results of sera diluted 1:10,000. Results indicated both mice were highly immunized against human HDL but mouse 1 had a higher concentration of specific antibody production against HDL.

TABLE VIII

Assay Results Using Mouse Polyclonal Antibodies to HDL

| Dilution | Mouse 1 | | Mouse 2 | |
|---|---|---|---|---|
| | Pre-Immune | Immune | Pre-Immune | Immune |
| 1:10 | 1284 | 6618 | 1793 | 8104 |
| 1:100 | 992 | 11,216 | 983 | 10,730 |
| 1:1000 | 579 | 12,411 | 1008 | 12,330 |
| 1:2500 | 491 | 12,649 | 978 | 11,462 |
| 1:5000 | 428 | 12,018 | 953 | 11,239 |
| 1:10000 | 367 | 11,417 | 706 | 9694 |

Table IX summarizes results obtained when media from hybridomas (culture supernatants) prepared from the spleen of mouse 1 (Table VIII) were tested for production of monoclonal antibody. The production of monoclonal antibodies specific for human HDL are indicated by a 50-fold increase over the negative control. Each of the five clones indicated in Table IX represents a single cell line producing a single monoclonal antibody against human apo A-I.

TABLE IX

Assay Results Using Mouse Monoclonal Antibodies to Human Apo A-I

| Negative | Clone 1 | Clone 2 | Clone 3 | Clone 4 | Clone 5 |
|---|---|---|---|---|---|
| 258 | 12682 | 13326 | 12757 | 12760 | 13541 | d) Determination of Mouse Anti-Human Apo A-I Monoclonal Antibody Specificity

Lipid was removed from HDL by diluting 1.0 ml of HDL in a solution of 10 ml chloroform, 10 ml methanol and 20 ml diethyl ether at 4° C. Apolipoproteins of HDL form a white precipitate which was collected by centrifugation at 10,000×g for 20 minutes at 4° C. The precipitate was washed once with 20 ml of diethyl ether and diethyl ether was removed by aspiration. The precipitate was warmed to about 35° C. to remove residual diethyl ether, and then dissolved in a solution of 0.067M 2-amino-2-hydroxymethyl-1,3-propanediol/HCl buffer, pH 6.8 containing 2%, w/v, sodium dodecyl sulfate, 10%, v/v, glycerol and 5%, v/v, 2-mercaptoethanol. After dissolving the apolipoprotein precipitate, the solution was heated to 100° C. for 3 minutes and allowed to cool to room temperature. Proteins in the solution were separated according to molecular weight by electrophoresis in sodium dodecyl sulfate as described for apo B in example 1d. Apolipoproteins of HDL separated on the acrylamide gel were transferred to a nitrocellulose fiber by electrophoresis. After the proteins were transferred to the nitrocellulose fibers, a thin strip was cut and stained to visualize the position of the protein bands for reference later. The remaining sheet was treated as described for apo B in 1d except that culture supernatants of individual hybidomas prepared against apo A-I were incubated with the strips overnight. Reaction of monoclonal antibody to the separated apolipoproteins of HDL transferred to the nitrocellulose strips was detected using alkaline phosphatase conjugated goat antimouse antibody as described in 1d. Apo A-I specificity of the monoclonal antibodies was determined by immunoreaction of apo A-I bands of characteristic molecular weight on the nitrocellulose strips.

e) Binding of Apo A-I to Iodipamide Ethyl Ester (IDE)

Iodipamide ethyl ester (IDE) particles were prepared by infusing two parts of an aqueous solution (0.1%, w/v) of polyvinyl pyrrolidone (15,000 MW) at a rate of 5 ml/minute into a cold (4° C.), rapidly stirred solution of one part IDE (5%, w/v) in dimethyl sulfoxide (DMSO) and one part ethanol. Immediately after the formation of the particles, 1.0 ml of human high density lipoprotein containing $^{125}$I-labeled apo A-I of a known protein specific activity [disintegrations per minutes per mg protein] and at concentrations between 0.5 microgram and 2.5 micrograms of protein per ml was added to 1.0 ml of IDE particles. The particles and proteins were mixed and then the particles were washed by addition of PBS containing human serum albumin at a concentration of 0.1%, w/v and centrifuged. After removing the washing solution by aspiration the particles were resuspended and washed again until radioactivity released into the wash was negligible (about four washes). The bound $^{125}$I-labeled apo A-I was then radioassayed and the mass of apo A-I bound by the IDE particles was calculated using the specific activity of the original $^{125}$I-labeled apo A-I (DPM/mg protein). The results are set forth in Table X.

TABLE X

Apolipoprotein A-I Bound to IDE Particles

| Micrograms Added | Micrograms Bound |
|---|---|
| 0.5 | 0.16 |
| 1.0 | 0.22 |
| 1.5 | 0.26 |
| 2.0 | 0.27 |
| 2.5 | 0.30 | f) Immunoassay of Apo A-I/IDE Particles Using Flow Cytometry

Iodipamide ethyl ester (IDE) particles with attached epitopes of apo A-I (A/IDE particles) were reacted with monoclonal antibodies specific for apo A-I by incubation overnight at 4° C. After incubation the particles were washed in PBS containing 0.1% bovine serum albumin and afterwards, the particles were reacted with biotin-conjugated sheep anti-mouse antibody and subsequently with fluoroscein-conjugated avidin for 30 minutes at room temperature as described in 1f. The Apo A-I/IDE particles were washed three times in PBS containing 0.1% bovine serum albumin and then fluorescent particles were analyzed using fluorescence-activated flow cytometry. Results are set forth in Table XI.

TABLE XI

Anti-Human Apo A-I Monoclonal Antibody Reactivity to Apo A-I/IDE Particles Using Fluorescence Activated Flow Cytometry

| Preparation | Mean Channel |
|---|---|
| IDE Particles Only | 30.1 |
| Neagtive Staining Control | 32.6 |

TABLE XI-continued

Anti-Human Apo A-I Monoclonal Antibody Reactivity to Apo A-I/IDE Particles Using Fluorescence Activated Flow Cytometry

| Preparation | Mean Channel |
| --- | --- |
| Irrelevant Monoclonal Antibody | 33.7 |
| Monoclonal Antibody to human Apo A-I (7.08.) | 41.3 |
| Monoclonal Antibody to human Apo A-I (7.18.) | 98.5 |

The fluorescence of the Apo A-I/IDE particles are assessed on a fluorescence per particle basis using this method. Results are expressed as the average or mean channel of fluorescence representing the average fluorescence per particle. The higher the channel, the more fluorescence per particle and the more monoclonal antibody bound to the particles. The scale is not linear but is logarithmic. Thus, the difference in the mean channel of the negative staining control, Apo A-I/IDE particles alone and irrelevant monoclonal antibody compared with the monoclonal antibodies specific for epitopes of human apo A-I of 9 and 66 clearly indicate that (1) epitopes of apo A-I were attached to the IDE particles; (2) the monoclonal antibodies reacted to the Apo A-I/IDE particles and (3) the reaction is specific for epitopes of Apo A-I. This example demonstrates that Apo A-I epitopes can be attached to a particles in such a way that the epitope reactivity for specific monoclonal antibodies is retained.

(5) Epitope-Specific Monoclonal Immunoassay of Apo A-I Bound to Polyvinyl Chloride All of the following procedures were performed in accordance with the procedures outlined in Example (4). High density lipoprotein (HDL) was isolated from human serum by high speed centrifugation and mouse anti-human HDL monoclonal antibodies were prepared from mice immunized with HDL. Hybridomas were screened for specific monoclonal antibody production to human HDL and apo A-I specificities of the monoclonal antibodies so prepared were determined.

a) Binding of Apo A-I to Polyvinyl Chloride

Labeled $^{125}$I-apo A-I (apo A-I) of a known protein specific activity [disintegrations per minutes per mg protein] and at concentrations between 0.49 mg/ml and 15.6 mg/ml in PBS was added to a 7.1 mm$^2$ surface of polyvinyl chloride. The solution was incubated overnight at 4° C. and then the surface was washed three times in 1%, w/v, BSA in PBS. After removing the washing solution by aspiration the surface bound $^{125}$I-apo A-I was radioassayed and its mass bound by the polyvinyl chloride was calculated using the specific activity of the original $^{125}$I-apo A-I. Results are set forth in Table XII.

TABLE XII

Binding of Human Apolipoprotein A-I to Polyvinyl Chloride

| Micrograms Added | Micrograms Bound |
| --- | --- |
| 0.49 | 0.021 |
| 0.98 | 0.038 |
| 1.95 | 0.060 |
| 3.90 | 0.082 |
| 7.80 | 0.099 |
| 15.60 | 0.118 | b) Immunoassay of Polyvinyl Chloride-Stabilized Epitopes of Apo A-I

A 7.1 mm$^2$ polyvinyl chloride surface was incubated with human HDL at a concentration of 1.5 μg/ml in 0.15M sodium carbonate/0.35M sodium bicarbonate, pH 9.0 at 4° C. After incubation the surface was washed three times in a solution of 1%, w/v, BSA in PBS and incubated in the same solution for 2 hours at room temperature. After incubation the liquid from the surface was removed by aspiration and 0.1 ml of a 1:250 dilution of the culture supernatant from a hybridoma producing monoclonal antibody to apo A-I was added. Immediately thereafter, 0.1 ml of human HDL was added containing 10 and 100 ng of apo A-I to compete with polyvinyl chloride stabilized epitopes of apo A-I. The mixture was incubated for 16 hours at 4° C. and then the surface was washed three times using a solution of 1%, w/v, BSA in PBS. Binding of the monoclonal antibody to polyvinyl chloride stabilized epitopes of apo A-I was detected by a final incubation with $^{125}$I-labeled sheep anti-mouse antibody. The results of the competition assay are presented below in Table XIII. The more added HDL-apo A-I the less radioactivity is bound to the polyvinyl chloride stabilized epitopes of apo A-I. The percent of bound to total counts added (Y-axis) can be graphed against the concentration of HDL to prepare a standard curve.

TABLE XIII

Competitive Immunoassay of Apo A-I Bound to a Polyvinyl chloride Surface and Human HDL Apo A-I Using an Anti-human Apo A-I Monoclonal Antibody

| Dilution | Bound DPM | % Total Counts |
| --- | --- | --- |
| Buffer Alone | 1900 | 100.0 |
| 1:100 | 1100 | 57.9 |
| 1:80 | 960 | 50.5 |
| 1:50 | 825 | 43.4 |
| 1:40 | 580 | 30.5 |
| 1:20 | 350 | 18.4 |
| 1:10 | 100 | 5.3 |

This invention is useful particularly for measuring the lipoprotein components associated with cholesterol, and includes a monoclonal based immunoassay kit for measuring the lipoprotein components in biological fluids to assess risk related to coronary artery disease complications.

In addition, the kit can include any other materials found useful in the description of this invention.

We claim:

1. Apolipoprotein attached to solid particles obtained by delipidating lipoprotein in the presence of said solid particles.

2. Apolipoprotein in accordance with claim 1 wherein said particles are iodipamide ethyl ester particles.

3. Apolipoprotein in accordance with claim 1 wherein said particles have a mean diameter in the range 1–100,000 nanometers with a coefficient of variation of less than 25%.

4. Apolipoprotein in accordance with claim 1 wherein said particles are polyvinyl chloride particles.

5. Apolipoprotein in accordance with claim 1 wherein said particles are polystyrene particles.

6. Apolipoprotein in accordance with claim 1 wherein said lipoprotein is high density lipoprotein.

7. Apolipoprotein in accordance with claim 1 wherein said lipoprotein is low density lipoprotein.

8. Apolipoprotein in accordance with claim 1 wherein said lipoprotein is very low density lipoprotein.

9. Apolipoprotein in accordance with claim 1 wherein said particles are selected from the group consisting of latex, starch, resin, esters and organic acids and organic bases which are insoluble in biological fluid.

10. Apolipoprotein in accordance with claim 1 wherein said solid particles with attached apolipoprotein are labeled with a detectable marker.

11. Apolipoprotein in accordance with claim 10 wherein said marker is a radioisotope.

12. Apolipoprotein in accordance with claim 1 wherein said apolipoprotein is apo B.

13. Apolipoprotein in accordance with claim 1 wherein said apolipoprotein is apo A-1.

14. A method of attaching apolipoprotein onto solid particles which comprises delipidating lipoprotein to produce said apolipoprotein in the presence of said solid particles.

15. A method in accordance with claim 14 wherein said lipoprotein is delipidated by a liquid lipid solvent.

16. A method in accordance with claim 14 wherein said apolipoprotein is apo B.

17. A method in accordance with claim 14 wherein said apolipoprotein is apo A-1.

18. A method in accordance with claim 15 wherein liquid lipid solvent is a mixture of dimethyl sulfoxide and ethyl alcohol.

19. A method in accordance with claim 15 wherein said liquid lipid solvent is a mixture of chloroform, methanol and diethyl ether.

* * * * *